(12) United States Patent
Chakrabartty et al.

(10) Patent No.: US 8,056,420 B2
(45) Date of Patent: *Nov. 15, 2011

(54) SELF-POWERED SENSOR

(75) Inventors: Shantanu Chakrabartty, Williamston, MI (US); Nizar Lajnef, Okemos, MI (US); Niell G. Elvin, East Lansing, MI (US); Amit S. Gore, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1003 days.

This patent is subject to a terminal disclaimer.

(21) Appl. No.: 11/895,635

(22) Filed: Aug. 24, 2007

(65) Prior Publication Data
US 2008/0047355 A1      Feb. 28, 2008

Related U.S. Application Data

(60) Provisional application No. 60/840,056, filed on Aug. 24, 2006.

(51) Int. Cl.
*G01B 7/16* (2006.01)
(52) U.S. Cl. .......................................... 73/777; 73/808
(58) Field of Classification Search ............. 73/760–860
See application file for complete search history.

(56) References Cited

U.S. PATENT DOCUMENTS

| 4,769,797 | A | 9/1988 | Murakami |
| 6,600,145 | B1 * | 7/2003 | Herz ...................... 250/214 SW |
| 7,741,177 | B2 * | 6/2010 | Wang ............................ 438/257 |
| 7,757,565 | B2 * | 7/2010 | Chakrabartty ................. 73/808 |
| 7,864,558 | B2 * | 1/2011 | Krieger ........................ 365/145 |
| 2002/0111756 | A1 | 8/2002 | Modgil |
| 2008/0047355 | A1 | 2/2008 | Chakrabartty et al. |

FOREIGN PATENT DOCUMENTS
EP   1863317   12/2007

OTHER PUBLICATIONS

N. Lajnef et al "A Piezo-Powered Floating-Gate Sensor Array for Long-Term Fatigue Monitoring in Biomechanical Implants", IEEE Transactions on Biomedical Circuits and Systems, IEEE, US vol. 2, No. 3; Sep. 1, 2008.
N. Najnet et al "Calibration and Characterization of Self-Powered Floating-Gate Sensor Arrays for Long-Term Fatigue Monitoring", Circuts and Systems, 2008, ISCAS 2008, May 18, 2008.

* cited by examiner

*Primary Examiner* — Max Noori
(74) *Attorney, Agent, or Firm* — Harness, Dickey & Pierce, P.L.C.

(57) ABSTRACT

A self-powered sensor is provided for fatigue monitoring and other low power requirement applications. The self-powered sensor is comprised of: a piezoelectric transducer; a non-volatile memory comprised of at least one floating gate transistor; and a current reference circuit adapted to receive a voltage signal from the piezoelectric transducer and operable to output an injection current into the non-volatile memory. The current reference circuit may employ a floating gate transistor operating in a weak-inversion mode.

19 Claims, 3 Drawing Sheets

SELF-POWERED SENSOR

CROSS-REFERENCE TO RELATED APPLICATIONS

This application claims the benefit of U.S. Provisional Application No. 60/840,056, filed on Aug. 24, 2006. The disclosure(s) of the above application(s) is (are) incorporated herein by reference.

FIELD

The present disclosure relates to a self-powered sensor.

BACKGROUND

Approximately 500,000 hip and knee replacements are performed each year in the United States. Although these implants exhibit excellent response during the initial rehabilitation period, fatigue and wear limits their success for long-term operation [1]. Monitoring of fatigue and wear has been previously shown to increase implant longevity by preventing mechanical failure through early intervention. Mechanical fatigue is the accumulation of damage in a structure under applied fluctuating stresses. Though the magnitudes of the applied stresses are less than the tensile strength of the material, the progressive fatigue damage may lead ultimately to mechanical failure. Fatigue life is defined as the number of load cycles necessary to induce failure and it depends on the level of fluctuating strain in the structure. Several fatigue prediction algorithms (e.g. Palmgren-Miner linear rule) rely on counting the number and magnitude of loading cycles applied to a structure. The fatigue in the structure can then be estimated using the cumulative statistics of these applied loads.

Piezoelectric transducers not only provide a mechanism for sensing fatigue in a structure but also can be used for self-powering of the sensors. Piezoelectric based self-powering for medical implants have several advantages over traditional battery powered techniques which suffer from limited life and complications due to biocompatibility. Poly-vinylidene diflouride (PVDF) is a piezoelectric plastic that is currently used for suture materials and has proven to be biocompatible. One disadvantage of PVDF is its very low mechano-electrical energy conversion. Such low power levels pose several challenges for designing self-powered sensors, which include:
1. Self-powered computation: Energy to perform sensing and computation on the sensor has to be harvested from the converted mechanical signal.
2. Non-volatile storage: All the parameters of internal state variables (intermediate and final) have to be stored on a non-volatile memory to account for unavailability of power (i.e. blackouts).
3. Sub-microwatt operation: All computation and storage functions have to be performed at sub-microwatt power dissipation levels to meet the power budget requirement of 1 µW.

The statements in this section merely provide background information related to the present disclosure and may not constitute prior art.

SUMMARY

A self-powered sensor is provided for fatigue monitoring and other low power requirement applications. The self-powered sensor is comprised of: a piezoelectric transducer; a non-volatile memory comprised of at least one floating gate transistor; and a current reference circuit adapted to receive a voltage signal from the piezoelectric transducer and operable to output an injection current into the non-volatile memory. The current reference circuit may employ a floating gate transistor operating in a weak-inversion mode.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
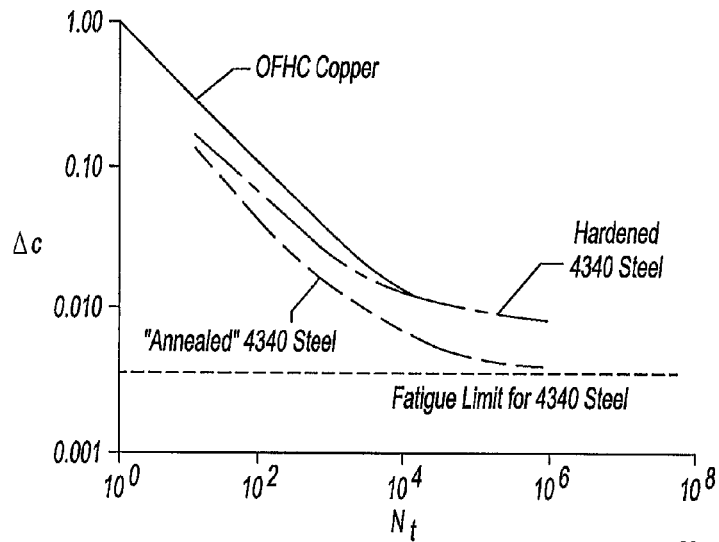
FIG. 1 is an exemplary S-N curve which can be used to estimate fatigue life.

Mechanical fatigue is the accumulation of damage in a structure under applied fluctuating stresses. Though the magnitudes of the applied stresses are less than the tensile strength of the material, the progressive fatigue damage may lead ultimately to mechanical failure. Fatigue life is defined as the number of constant amplitude load cycles necessary to induce failure in an initially undamaged component. Generally, the fatigue life of a mechanical component under cycling applied load depends on the level of fluctuating strain in the structure. With reference to FIG. 1, this can be represented by the S-N curve, which is obtained using experimental measurements. In the S-N curve, S is the mechanical strain level ($\Delta\epsilon$) in the component under a harmonic load, and N is the number of cycles that causes failure of the component at that strain level.

The S-N curves can be used directly to estimate the fatigue life under constant amplitude harmonic load conditions. However, in most applications the applied load is not cyclic. The simplest approach to model fatigue behavior under variable amplitude load condition involves the concept of cumulative damage, which can be described using the Palmgren-Miner linear rule:

$$\sum_{i=1}^{m} \frac{n_i}{N_{fi}} = 1 \quad (1)$$

where $n_1$ denotes total number of events when the electric signal generated by the piezoelectric transducer exceeded a threshold $a_i$. Miner's rule assumes that each strain cycle of a given magnitude consumes $1/N_{fi}$ of the total fatigue life, where $N_{fi}$ is the fatigue life of the specimen at the given strain amplitude (obtained from the S-N curve). A major step in the implementation of this approach is the identification of different loading events that contribute to fatigue damage. Counting algorithms are used to reduce any loading spectra to a series of equivalent stress-strain states. The experimental data for each stress-strain state is implemented with the Palmgren-Miner's rule to provide a summation of fatigue damage. Several empirical cycle counting methods have been developed for different applications. For the purpose of this study, a modified level-crossing peak counting method is used. This method consists of detecting and summing the maximum level reached by different peaks of the applied strain function. It is readily understood that other counting methods may be employed.

Figure 2:
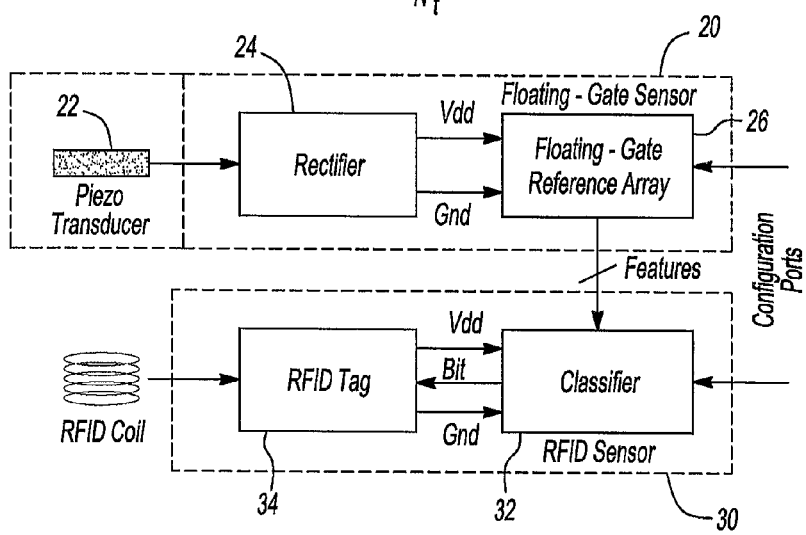
FIG. 2 is a system level architecture of an exemplary fatigue monitoring system.

FIG. 2 illustrates a system level architecture of an exemplary fatigue monitoring system 20. The fatigue monitoring system 20 is comprised of a piezoelectric transducer 22, a rectifier 24 and a floating gate sensor 26. The piezoelectric transducer 22 may be operably coupled to a structure being monitored, such as a medical implant. Stress applied to the monitored object causes the piezoelectric transducer 22 to generate a voltage signal While reference is made throughout this disclosure to medical implants, it is readily understood that the fatigue monitoring system has other applications (e.g., monitoring structural integrity of aircraft or vehicle components).

The floating gate sensor 26 continuously records the output of the piezoelectric transducer 22. The full-wave rectifier 24 interposed between the piezoelectric transducer 22 and the floating gate sensor 26 generates un-regulated supply voltages (vdd and gnd) from the signal output by the transducer 22. In an exemplary embodiment, the full wave rectifier 24 is implemented using a standard diode bridge. For the prototype described below, n+− p-substrate and p+− n-well diodes were used, which naturally occur using electrostatic discharge (ESD) diodes. The supply voltages are used by a floating gate sensor 26 to compute the amplitude and duration statistics of the rectified signal. The floating gate sensor 26 then updates the internal variables which represent cumulative history of the mechanical strain cycles experienced by the monitored structure. The floating gate sensor is self-powered and extracts all its operational energy from the rectified signal.

The floating gate sensor 26 may interface an RFID sensor 30 that is used to interrogate and/or download the recorded statistics. The RFID sensor 30 embeds a classifier 32 that uses the statistics as features to produce a confidence value proportional to time-to-failure. An RFID interface 34 is then used to transmit the confidence value to an external interrogator. The powering and operation of the RFID-subsystem is completely asynchronous and derives its power through RF coupling from an external interrogator.

Figure 3:
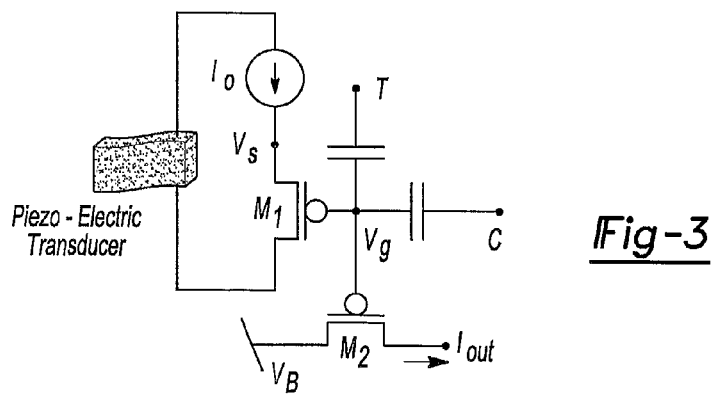
FIG. 3 is a simplified circuit model for a floating gate sensor.

A simplified circuit model for the proposed floating gate sensor 22 is shown in FIG. 3. It consists of a floating gate (denoted by voltage $V_g$) which is coupled to the gates of an injection transistor M1 and a read-out transistor M2. The current delivered by the piezo transducer is limited by a current reference ($I_0$) which biases the transistor M1 in weak-inversion. The nodes C and T represent control and tunneling terminals. In weak-inversion, the expression for source current through the pFET transistor M1 is given by:

$$I_0 = I_s e^{-\kappa \frac{V_g}{U_T}} e^{\frac{V_s}{U_T}}$$

where $I_0$ is the source current, $I_s$ is a pre-exponential current, $V_g$ is the floating gate voltage, $\kappa$ is the coupling coefficient from floating gate to channel, $U_t$ is the thermal voltage. For the fixed reference current $I_0$, the gate current of M1 due to impact ionized hot-electron injection (IHEI) is given by:

$$I_g = \beta I_0 e^{\frac{V_s}{V_{inj}}} = -C \frac{\partial V_g}{\partial t}$$

where $\beta$ and $V_{inj}$ are constants, and C is the total capacitance at the floating gate. Using equations (1) and (2), the following expression for $V_g$ is obtained as a function of time:

$$V_g(t) = -\frac{1}{K_2} \log\left(K_1 K_2 \left(t + \frac{1}{K_1 K_2} e^{-K_2 V_{g0}}\right)\right)$$

where $$K_1 = \left(\frac{\beta I_0}{C}\right)\left(\frac{I_0}{I_s}\right)^{\frac{U_t}{V_{inj}}}$$

$$K_2 = \frac{\kappa}{V_{inj}}$$

and $V_{g0}$ is the initial gate voltage.

Figure 4:
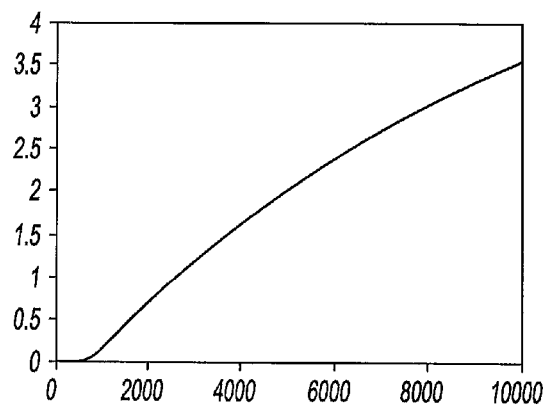
FIG. 4 is a graph of the read out current from a floating gate sensor over time.

The floating gate voltage is mapped onto a read-out current $I_{out}$ using the transistor M2. Because transistor M2 may not be in a weak-inversion we use an EKV model to compute the output current $I_{out}$ as:

$$I_{out} = a^2 \log^2\left(1 + \alpha e^{\frac{-\kappa V_g + V_B}{U_T}}\right)$$

where $\alpha$ and a are parameters of the model. FIG. 4 plots the read-out current $I_{out}$ over time for parameters a and $\alpha$, obtained experimentally. It can be seen from the model that the response of the circuit is monotonic and exhibits a saturating response. Therefore the model in FIG. 3 could be used for calculating the total cumulative time a piezo-transducer was able to deliver a load of current $I_0$, which will be proportional to the cumulative stress period applied to the implant.

Figure 5:
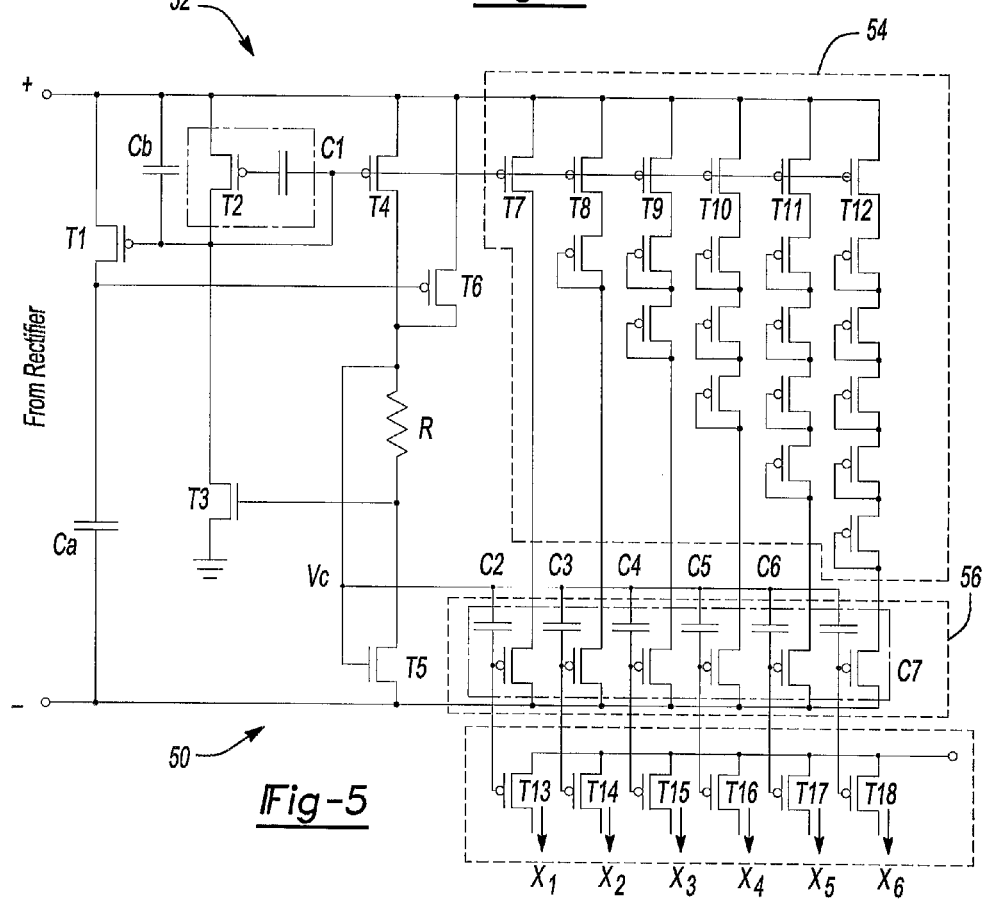
FIG. 5 is a schematic of an exemplary implementation of a floating gate sensor.

FIG. 5 illustrates an exemplary implementation of a floating gate sensor 50. The floating gate sensor 50 is comprised of a current reference circuit 52, a driving circuit 54 and a storage circuit 56. Each of these circuits are further described below.

In an exemplary embodiment, the reference current circuit 52 is implemented using transistors T1-T5 and resistor R. In a standard current reference circuit, the ratio of the PMOS current mirror transistors along with R determines the magnitude of the reference current. This exemplary implementation uses a floating gate transistor T2 coupled to a gate of transistor T1. The reference current is determined by the charge injected onto the floating gate T2 and the resistor value R. When all the transistors T2-T5 are biased in weak-inversion (i.e., operating in a sub-threshold mode), the reference current through T4 is given by $$I_{ref} \approx \frac{Q_f}{C_f R}$$

where $Q_f$ is the charge stored on the floating gate C1 and $C_f$ is the total floating gate capacitance. By accurately controlling the amount of floating gate charge, $Q_f$, small increments of reference current can be generated. The charge on the gate can be modified using hot electron injection or through tunneling. Injection adds electrons to the floating gate as a result its potential decreases which leads to an increase in the drain current through the transistor. For a PMOS transistor biased in weak-inversion drain-to-source voltages greater than 4.5V has been found to be sufficient for injection. Of note, the current reference circuit is able to compensate for temperature variations, as evident from reference current expression which is independent of temperature dependent parameters. Temperature compensation due to the current reference circuit has been validated through simulation and exhibits less than 2% variation over a 70° C. variation in temperature. Even though this feature is not required during normal operation of the implantable device, it has been observed that for some implants (hip implants) repeated wear and tear can dramatically increase in ambient temperature. While a particular circuit configuration was described above, it is readily understood that other circuit configurations, preferably having at least one floating gate transistor, may be used for the current reference circuit.

In the exemplary embodiment, a storage capacitor $C_a$ was used at the output of the rectifier to filter out unwanted high-frequency components. The size of the capacitor provides a trade-off between total discharge time versus the voltage swing at the sensor. For the prototype an external capacitor (10 nF) was chosen which led to voltage swing of up to 8V for 20V generated by the piezoelectric transducer. A voltage over-protection and clamping circuitry was integrated at the output of the diode bridge to prevent damage due to unwanted piezoelectric surges.

The storage circuit 56 is an array of floating gate transistors C2-C6 which provide non-volatile storage. A floating gate is a poly-silicon gate surrounded by an insulator, which in standard semiconductor fabrication process is silicon-dioxide. Because a floating gate is surrounded by high quality insulation any electrical charge injected onto this gate is retained for long intervals of time (>8 years). In the exemplary embodiment, each floating gate transistor C2-C6 also has a tunneling capacitor which is used for removing electrons (erase operation) from the gate. It is envisioned that other types of storage circuits are within the broader aspects of this disclosure.

An exemplary driving circuit 54 is interposed between the current reference circuit 52 and the array of floating gate transistors 56. In this exemplary circuit, transistors T7-T12 mirror the current in T4 to drive the floating gate transistors C2-C7. More specifically, the driving circuit is comprised of a plurality of circuit branches, where each circuit branch electrically couples to a different floating gate transistor in the array of floating gate transistors. Voltage drop in each branch will be controlled using diode connected PMOS transistors and will ensure different drain-to-source voltage across each of floating gate cells C2-C7. During the pre-calibration stage each of the floating gate cells are programmed (using tunneling and injection) to store a fixed amount of charge, hence a fixed gate voltage across C2-C7. When a rectified voltage is presented across the supply terminals (+−), the circuit generates a reference current and a stable voltage reference at node Vc. Depending on the magnitude of the rectified voltage, different cells C2-C7 start injecting charge on its floating gate. Likewise, other circuit configurations are envisioned for the driving circuit.

Figure 6:
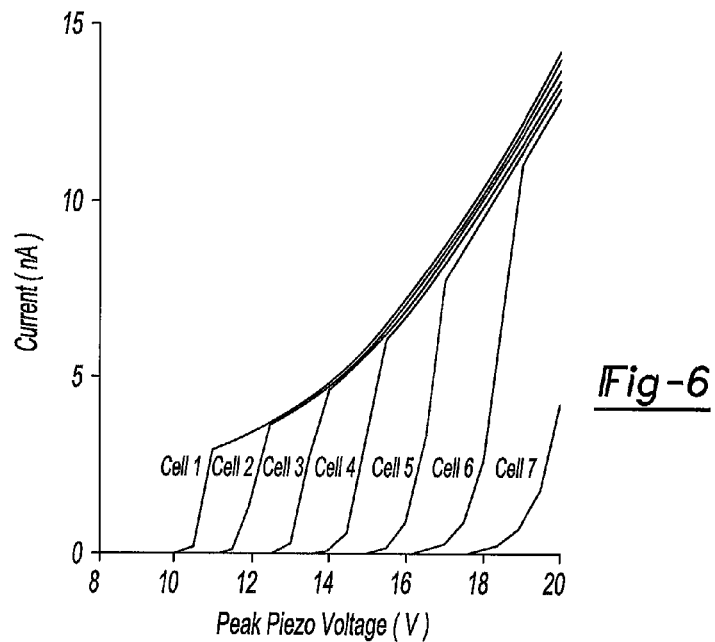
FIG. 6 is a graph illustrating simulation results obtained using the floating gate sensor.

SpectreS based spice simulation of the current reference circuit demonstrates an activation profile of different floating gate cells C2-C7 at different peak amplitude as show in FIG. 6. For this experiment a storage capacitor of 10 nF was chosen, and the duration of the piezoelectric pulse excitation was set to 2 seconds. The circuit exhibits a start-up time of 100 ms, which is sufficient for most structural engineering applications. The start-up however can be optimized by appropriately sizing the storage capacitor at the rectifier but at the expense of lower coupling voltage (rectifier). The simulation also shows poor current regulation of the reference circuit due to sub-threshold operation of the circuit but does not adversely affect the response of the sensor.

The results indicate that different floating gate cells in the array start injecting at different piezoelectric potential and therefore record cumulative amplitude statistics of signal. The architecture therefore implements a self-powered flash-data converter. The total charge accumulated on the floating gate is measured by sensing the current through the read-out transistors T13-T18. The transistors T13-T18 act as read-out transistors that are used to quantify the stored charge on floating gates C2-C7 by measuring the drain currents flowing through T13-T18. The read-out transistors are powered by an external interrogator by transferring energy via physical inter-connections or via RF coupling. Thus the sub-circuit enclosed in the dotted line in FIG. 5 is to be implemented in the RFID sensor subsystem in FIG. 2. The drain currents through transistors T13-T18 represents a feature vector encoding the history of stress-strain patterns and is used by a classifier to generate time-to fail confidence scores.

A prototype floating-gate sensor was fabricated in a standard 0.5 µm CMOS process. The floating gate transistors were designed using a double polysilicon transistor with a minimum injection potential of 4.2V and an erase voltage of 15V. For preliminary experiments, a signal generator was used to simulate the functionality of a piezoelectric transducer. Different voltage levels were applied at the floating gate array input and the read-out current through transistor T13 was measured.

Figure 7:
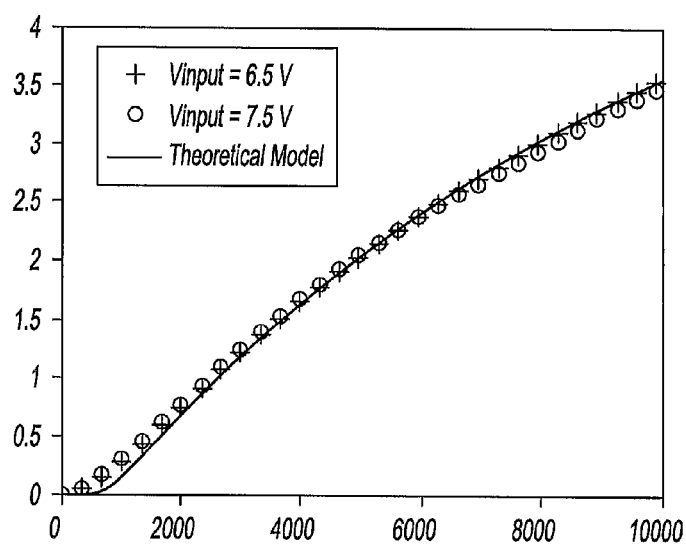
FIG. 7 is a graph depicting the measured response of the single floating gate reference element.

FIG. 7 shows the current measured through transistor T13 for different voltages against the total duration of the applied input. The injection profiles for different voltages are relatively close to each other due to current reference based injection architecture. The response is monotonic and approximately linear which demonstrates that the sensor can be used for computing total strain cycles experienced by a mechanical structure. The total power dissipated during the entire experiment was measured to be 320 nW which is well below the power generated by a PVDF transducer (1 µW). For long term monitoring it is critical that the measured current show a compressive non-saturating response (equivalent to logarithmic response). Long term monitoring experiments with the floating gate sensor have shown non-saturating response for up to $10^5$ seconds demonstrating the effectiveness of current limiting transistors T7 in FIG. 5.

In this disclosure, the feasibility of a self-powered fatigue measuring system based on a combination of piezoelectric transduction and floating gate injection was demonstrated. Preliminary results indicate that the response of the sensor is proportional to an equivalent total number of stress cycles experienced by a structure. The total power dissipation of the sensor is less than 1 µW. The above description is merely exemplary in nature and is not intended to limit the present disclosure, application, or uses.

What is claimed is:
1. A self-powered sensor, comprising:
  a piezoelectric transducer;
  a non-volatile memory comprised of at least one floating gate transistor; and a current reference circuit having a floating gate transistor operating in a weak-inversion mode, the current reference circuit adapted to receive a voltage signal from the piezoelectric transducer and operable to output an injection current into the non-volatile memory.

2. The self-powered sensor of claim 1 wherein the current reference circuit is arranged as a current mirror comprised of two transistors, where the floating gate transistor is coupled between gate nodes of the two transistors and source nodes of the two transistors.

3. The self-powered sensor of claim 1 wherein the non-volatile memory is comprised of an array of floating gate transistors.

4. The self-powered sensor of claim 3 further comprises a driving circuit interposed between the reference current circuit and the array of floating gate transistors and operable to inject a charge onto different floating gate transistors of the array based on a magnitude of the voltage signal.

5. The self-powered of claim 4 wherein the driving circuit is comprised of a plurality of circuit branches, where each circuit branch electrically couples to a different floating gate transistor in the array of floating gate transistors.

6. The self-powered sensor of claim 5 wherein each circuit branch defines a different current threshold, whereby a charge is injected onto the floating gate transistor associated with a given circuit branch when the magnitude of the reference current exceeds the current threshold for the given circuit branch.

7. The self-powered sensor of claim 1 further comprises a full wave rectifier interposed between the piezoelectric transducer and the current reference circuit.

8. The self-powered sensor of claim 1 wherein the piezoelectric transducer is operably coupled to a medical implant, such that total charge stored in the non-volatile memory is proportional to loading cycle applied to the medical implant.

9. The self-powered sensor of claim 1 wherein the piezoelectric transducer is comprised of a polyvinylidene fluoride material.

10. A self-powered sensor, comprising:
a current reference circuit adapted to receive a voltage signal and operable to output a reference current compensated for temperature variations;
an array of floating gate transistors which provides non-volatile storage; and
a driving circuit interposed between the current reference circuit and the array of floating gate transistors and operable to inject a charge into select transistors of the array of floating gate transistors based on a magnitude of the voltage signal.

11. The self-powered sensor of claim 10 wherein the current reference circuit having a floating gate transistor such that a magnitude of the reference current is determined by a charge injected onto the floating gate transistor.

12. The self-powered sensor of claim 10 wherein the current reference circuit is arranged as a current mirror comprised of two transistors, where the floating gate transistor is coupled between gate nodes of the two transistors and source nodes of the two transistors.

13. The self-powered of claim 10 wherein the driving circuit is comprised of a plurality of circuit branches, where each circuit branch electrically couples to a different floating gate transistor in the array of floating gate transistors.

14. The self-powered sensor of claim 13 wherein each circuit branch having a different voltage drop such that a charge is injected into the floating gate transistor coupled to a given circuit branch when the voltage signal exceeds the voltage drop of the given circuit branch.

15. The self-powered sensor of claim 10 wherein signals applied to gate nodes of the floating gate transistors in the array of floating gate transistors is derived from the voltage signal.

16. The self-powered sensor of claim 10 further comprises a capacitor coupled to gate nodes of each transistor in the array of floating gate transistors.

17. The self-powered sensor of claim 10 wherein the voltage signal is received from a piezoelectric transducer.

18. The self-powered sensor of claim 10 further comprises an array of read-out transistors coupled to the array of floating gate transistors and operable to measure charge stored in the array of floating gate transistors.

19. A self-powered sensor, comprising:
a piezoelectric transducer;
a non-volatile memory comprised of at least one floating gate transistor; and
a current reference circuit adapted to receive a voltage signal from the piezoelectric transducer and operable in a weak-inversion mode to output an injection current into the non-volatile memory, thereby recording output of the piezoelectric transducer.

* * * * *

UNITED STATES PATENT AND TRADEMARK OFFICE
CERTIFICATE OF CORRECTION

PATENT NO. : 8,056,420 B2  
APPLICATION NO. : 11/895635  
DATED : November 15, 2011  
INVENTOR(S) : Shantanu Chakrabartty et al.

Page 1 of 1

It is certified that error appears in the above-identified patent and that said Letters Patent is hereby corrected as shown below:

In the Specifications:

Column 3, line 22, after "signal" insert --.--.

Column 4, line 53, "PMOS" should be --pMOS--.

Column 5, line 8, "PMOS" should be --pMOS--.

Column 5, line 54, "PMOS" should be --pMOS--.

Column 6, line 1, "show" should be --shown--.

In the Claims:

Column 7, line 19, Claim 5, after "self-powered" insert --sensor--.

Column 8, line 13, Claim 13, after "self-powered" insert --sensor--.

Signed and Sealed this
Fourteenth Day of May, 2013

Teresa Stanek Rea
*Acting Director of the United States Patent and Trademark Office*